(12) United States Patent
Satomi et al.

(10) Patent No.: US 8,895,141 B2
(45) Date of Patent: *Nov. 25, 2014

(54) EXCIPIENT FOR COMPRESSED TABLETS COMPRISING NOVEL SPHERICAL MANNITOL

(75) Inventors: Jin Satomi, Shizuoka (JP); Maki Imaoka, Shizuoka (JP)

(73) Assignee: Mitsubishi Shoji Foodtech Co., Ltd., Tokyo (JP)

( * ) Notice: Subject to any disclaimer, the term of this patent is extended or adjusted under 35 U.S.C. 154(b) by 34 days.

This patent is subject to a terminal disclaimer.

(21) Appl. No.: 12/737,789

(22) PCT Filed: Aug. 14, 2009

(86) PCT No.: PCT/JP2009/064334
§ 371 (c)(1),
(2), (4) Date: Feb. 16, 2011

(87) PCT Pub. No.: WO2010/021300
PCT Pub. Date: Feb. 25, 2010

(65) Prior Publication Data
US 2011/0135927 A1    Jun. 9, 2011

(30) Foreign Application Priority Data
Aug. 18, 2008  (JP) .................. 2008-209851

(51) Int. Cl.
| | |
|---|---|
| *B32B 5/16* | (2006.01) |
| *A61K 9/20* | (2006.01) |
| *A61K 47/26* | (2006.01) |
| *A61K 9/16* | (2006.01) |

(52) U.S. Cl.
CPC .............. *A61K 9/2018* (2013.01); *A61K 47/26* (2013.01); *A61K 9/1623* (2013.01)
USPC ......................... 428/402; 424/465; 568/852

(58) Field of Classification Search
CPC ..... A61K 47/26; A61K 9/2018; A61K 9/1623
USPC .......................................... 428/402; 568/852
See application file for complete search history.

(56) References Cited

U.S. PATENT DOCUMENTS

| | | |
|---|---|---|
| 3,145,146 A | 8/1964 | Lieberman et al. |
| 6,264,989 B1 | 7/2001 | Kato et al. |
| 2010/0167052 A1* | 7/2010 | Satomi et al. .................. 428/402 |

FOREIGN PATENT DOCUMENTS

| | | |
|---|---|---|
| JP | 39-642 B | 1/1964 |
| JP | 61-085330 A | 4/1986 |

(Continued)

OTHER PUBLICATIONS

Elversson et al. "Particle Size and Density in Spray Drying-Effects of Carbohydrate Properties", Journal of Pharaceutical Sciences, Published Sep. 2005 (pp. 2049-2060).*

(Continued)

Primary Examiner — Gary Harris
(74) Attorney, Agent, or Firm — Rader, Fishman & Grauer PLLC

(57) ABSTRACT

[Problem to solve] To provide an excipient for compressed tablets capable of diluting active components in the industries of foodstuffs, medicines, etc. applicable to various tablets like disintegrating agents, troches, etc., largely avoiding the conventional compressing troubles about mannitol like capping, sticking, etc., thereby assuring a high tablet hardness.

[Means to solve the problem] An excipient for compressed tablets characterized in that it comprises spherical particles of crystalline mannitol having an aspect ratio of 1.0 to 1.2 and according to Test A, absorption rate 1 of 25 to 60% and absorption rate 2 of 15 to 40%.

3 Claims, 2 Drawing Sheets

(56) References Cited

FOREIGN PATENT DOCUMENTS

| | | | | |
|---|---|---|---|---|
| JP | 11092403 A | * | 4/1999 | ............ A61K 47/36 |
| JP | 2003-192585 A | | 7/2003 | |
| JP | 2005-510497 A | | 4/2005 | |
| JP | 2005-306770 A | | 11/2005 | |
| JP | 2006-028130 A | | 2/2006 | |
| WO | WO-03/035036 A1 | | 5/2003 | |
| WO | WO 2008146590 A1 | * | 12/2008 | |

OTHER PUBLICATIONS

International Search Report mailed on Sep. 8, 2009.

Communication from European Patent Office for application No. 087525291.1 dated May 10, 2012.

Elversson, et al., "Particle Size and Density in Spray Drying-Effects of Carbohydrate Properties", Journal of Pharmaceutical Sciences, vol. 94, No. 9, Sep. 2005, pp. 2049-2060.

* cited by examiner

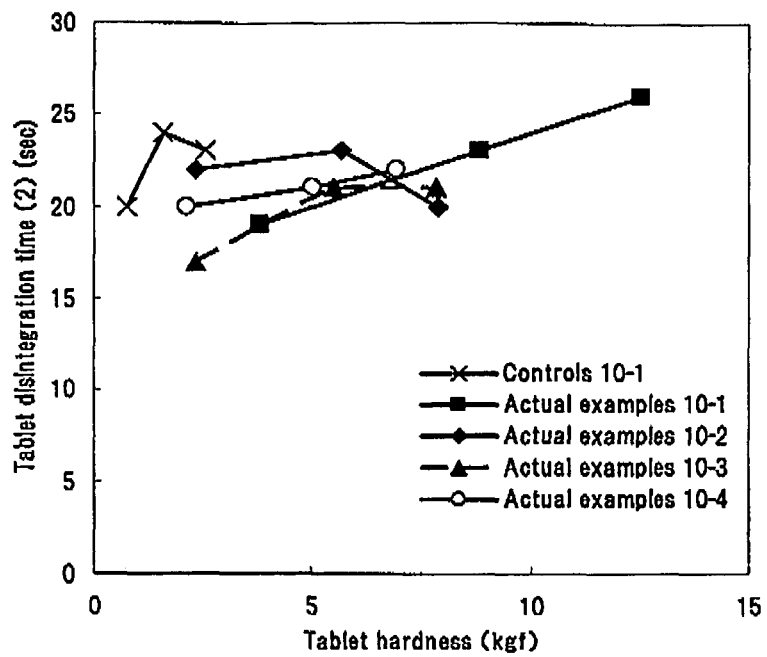
Fig.1. Tablet hardness and tablet disintegration time (2) of actual examples 10-1-1 to 10-4-3, and controls 10-1-1 to 10-1-3

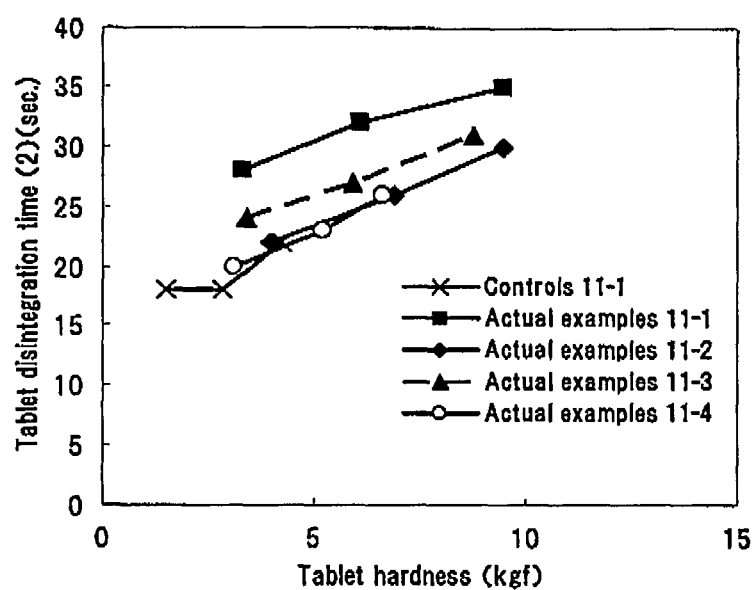
Fig.2. Tablet hardness and tablet disintegration time (2) of actual examples 11-1-1 to 11-4-3, and controls 11-1-1 to 11-1-3

EXCIPIENT FOR COMPRESSED TABLETS COMPRISING NOVEL SPHERICAL MANNITOL

TECHNICAL FIELD

The present invention relates to an excipient for compressed tablets comprising spherical particle of crystalline mannitol made by spray drying.

BACKGROUND ART

In solid preparations such as tablets, pills, granules, powders, fine particles, troches, masticatories, etc. in the industries of medicines, foodstuffs, etc., additives such as excipients, stabilizers, preservatives, buffers are used in order to stabilize the active components, the shape of the preparation per se or to improve the usefulness. Such additives must be harmless in the ingestion in the above preparations and should not inhibit the effects of the active components of the preparations or not be of a hindrance to tests.

Conventional solid preparations contain various types of excipients such as starches like potato starch, corn starch, etc., sugars like lactose, sucrose, glucose, etc., inorganic salts like calcium phosphate, precipitated calcium carbonate, etc., for the purpose of diluting the active components. Soluble saccharides in particular can be widely used as excipients e.g. for troches, masticatories or sublingual tablets.

Among such saccharides, lactose is widely used as an excipient, thanks to its high stability under high humidity condition and the easy handling when making tablets. However, lactose has many problems as mentioned below.

One of the problems of lactose consists in its insufficient hardness when compressed, due to the loose binding among the crystal particles, when used as an additive as crystallized in making tablets.

Japanese Laid-Open Patent No. 6-205959 refers to granules, saying "A spherical granule comprises 95% by weight or more of lactose, and has a long diameter/short diameter ratio of 1.2 or less, and, as an assembly, a bulk density of 0.7 g/ml or more and an angle of repose of 35° or less. The spherical granule is made by feeding lactose particles into a granulating and coating apparatus equipped with a horizontal rotary disk having a smooth surface to contact with the granules, and by spraying lactose solution while the above-mentioned rotary disk is rotated". However, tablets made of granules manufactured in this way cannot be sufficiently hard, while it takes much time to disintegrate, despite such insufficient hardness, thereby failing to be a satisfactory excipient for compressed tablets.

Japanese Laid-Open Patent No. 62-265295 refers to "Spray dried lactose products obtained by feeding a slurry of crystalline α-lactose hydrate in a saturated lactose solution to a spray drier and drying the same, in which less than 50% by weight of the lactose is in amorphous form and at least 50% by weight of the crystalline part consists of particles of 50 µm or less". However, when used as an excipient for compressed tablets, this spray dried lactose shifts in its amorphous part to a stable crystalline state, due to compression energy when making tablets, absorbing or releasing moisture, to change the hardness of tablets greatly, thereby failing to be a satisfactory excipient for compressed tablets.

Moreover, lactose is highly reactive due to the hemiacetal structure in the molecule, to produce a brown reactant, particularly in the presence of active components having primary amino groups, by Maillard reaction resulting from reaction between carbonyl and amino groups. It is known that vitamin $D_3$ derivatives in particular are remarkably decomposed when blended with lactose. Moreover, when the active components are acid, lactose has a disadvantage of disaccharide to be spited on hydrolysis into glucose and galactose, losing the properties of lactose, thereby failing to be a satisfactory excipient for compressed tablets also in terms of chemical stability with active components.

On the other hand, mannitol deserves mention as another saccharide equivalent to lactose in good stability under high humidity condition (high critical relative humidity). D-mannitol, a kind of hexitol, is widely used for various types of foodstuffs, medicinal bases, tablet or powder excipients, etc. thanks to its properties excellent in stability under high humidity condition, usually in the form of white crystalline powder, odor-free, mildly tasting as sweet as 60 to 70% of sucrose to have the effect of masking bitterness, less caloric than sucrose or glucose, safe to users, etc. also enabling use of highly reactive active components, unlike lactose, thanks to its chemical stability.

However, crystal particles of mannitol just having crystallized out from water are loosely bound to one another, as in the case of lactose, failing to be hard enough, when directly compressed, to keep the tablets from collapsing during transport. In addition, its fine crystalline spiculae are poor in fluidity, to cause capping, sticking, etc. when compressed, failing to enable continuous compressing.

Diverse methods for producing mannitol particles utilizable as various excipients have been proposed for the purpose of overcoming the drawbacks of crystallized mannitol as excipient for compressed tablets.

The specification of Japanese Patent No. 3447042 discloses "A process for producing a spherical particle comprising a granulated particle containing at least 95 wt % of a water-soluble single substance which has a viscosity of 10 cps or less as determined in the form of a saturated aqueous solution, the spherical particle having an aspect ratio of 1.2 or less and, as an assembly, having a bulk density of 0.65 g/ml or more and an angle of repose of 35 degree or less", referring to D-mannitol as an example of "water-soluble single substance".

The specification of Japanese Patent No. 3491887 discloses "a process for producing a sugar alcohol granule assembly for direct compression processing, in which 95 wt % or more of the assembly is present as particles of 710 µm or less and 50 wt % or more of the assembly as those of 75 to 710 µm, and the assembly has a bulk density of 0.5 g/ml or more and an angle of repose of 40 degree or less, the process comprising the steps of charging a powder having a sugar alcohol content of 95% by weight or more into a fluidized-bed granulating and coating apparatus; fluidizing the powder with fluidized air fed into the vessel; spraying an aqueous solution to granulate the powder; and sifting it through a sieve", referring to D-mannitol as an example of "sugar alcohol".

The specification of Japanese Patent No. 3910939 discloses "a spherical particle comprising an assembly of particles containing at least 95% by weight of a water-soluble single substance, the spherical particle having an aspect ratio of 1.2 or less and, as an assembly, having a bulk density of 0.65 g/ml or more, an angle of repose of 35 degree or less, wherein:
a) the single substance is one selected from the group consisting of a sugar alcohol, vitamin C and sodium chloride;
b) a saturated aqueous solution of the single substance has a viscosity of 10 cps or less at temperatures of 25 to 45° C.;
c) the spherical particle has an abrasiveness of 1.0% or less", referring to D-mannitol as an example of "sugar alcohol"

The specification of Japanese Laid-Open Patent No. 7-184590 discloses "a process for preparing a relatively pure powdered mannitol having, a non-excessive and reduced friability of between 40 and 80% in a test I, a low apparent density of between 300 and 525 g/l for a particle size fraction (omitted) of, between 100 and 200 microns, and in addition a special particle size distribution in the sense that it contains less than 30% of particles smaller than 75 microns, the process comprising the steps of spraying a mannitol solution or suspension and granulating by wet route the mannitol obtained at the spraying step".

The processing techniques adopted in the above four specifications are all based on granulation. Granulation here means a method of precipitating solid ingredients by agglomeration of surrounding mannitol particles around core mannitol particles, by means of appropriate solvents or solution as needed, e.g. drying the surroundings or a combined use of such methods, at any rate, in order to grow the raw material powder gradually into big agglomerations.

Needle crystals like those of mannitol, used as raw material powder, are made into heavy particles filled up with crystals densely even inside, tending to have a large particle diameter, failing to respond to the need for light and fine particles such as in the case of excipients required to have fluidity of particles.

As an example of directly compressed product made by granulation, Pearlitol is now on sale from ROQUETTE FRERES, however, still leaving room for improvement as an excipient in the insufficient hardness and high hygroscopicity of made tablets.

The specification of Japanese Laid-Open Patent No. 2004-2290 discloses "a process for the preparation of directly compressible mannitol having a content of the β modification of greater than 90%, in which a) in a first step, an aqueous D-mannitol solution as starting material, spray gas, pulverulent β-mannitol and hot gas are combined, b) the resultant pulverulent product is precipitated into a fluidized bed, taken up, fluidized and transported further". However, the same specification makes no reference to the made particles, nor to their properties or to the tablets made with the particles.

On the other hand, crystallized mannitol (trade name: Parteck M200) made by granulation as a direct compressing excipient is now on sale from Merck, however, still leaving room for improvement as an excipient in the high hygroscopicity of tablets made of this product.

Therefore, particles of crystalline mannitol have so many problems still remaining unsolved, when used as an excipient for medicinal preparations.

SUMMARY OF THE INVENTION

Problems to be solved by the Invention

The object of the present invention consists in offering an excipient for medicinal preparations capable of diluting active components in the industries of foodstuffs, medicines, etc., utilizable for various kinds of tablets like disintegrating agents, troches, etc., lessening the likelihood of compressing troubles e.g. like capping, sticking so far arising about the use of mannitol, while assuring sufficiently high tablet hardness. Such an excipient is highly stable against active components in tablet, also avoiding the troublesome issues so far surrounding the use of lactose.

Means to Solve the Problems

The present inventors worked hard to attain the above object and found out that spherical particles of crystalline mannitol having an extremely high sphericity, a high oil absorption rate and a low bulk density, obtained by fine-tuning the rates of crystallization and moisture vaporization, should be used as an excipient combining useful properties for medicinal preparations, resulting in completion of the present invention. Then, the object of the present invention can be attained by the following means.

First, an excipient for compressed tablets characterized in that it comprises spherical particles of crystalline mannitol having an aspect ratio of 1.0 to 1.2, and having according to Test A, an oil absorption rate 1 of 25 to 60% and an oil absorption rate 2 of 15 to 40%.

Second, an excipient for compressed tablets according to the above first, characterized in that it comprises spherical particles of crystalline mannitol having a mean diameter of 15 to 165 µm and, as a powder, a loose bulk density of 0.35 to 0.60.

Third, an excipient for compressed tablets according to the above first or second, characterized in that it comprises spherical particles of crystalline mannitol having a mean diameter of 15 to 165 µm and, as a powder, an angle of repose of 30 to 50 degrees.

Fourth, an excipient for compressed tablets according to the above first, characterized in that it comprises spherical particles of crystalline mannitol having a mean diameter of 15 to 85 µm and, as a powder, a loose bulk density of 0.35 to 0.60.

Fifth, an excipient for compressed tablets according to the above first or fourth, characterized in that it comprises spherical particles of crystalline mannitol having a mean diameter of 15 to 85 µm and, as a powder, an angle of repose of 30 to 50 degrees.

Sixth, an excipient for compressed tablets according to the above first, characterized in that it comprises spherical particles of crystalline mannitol having a mean diameter of 20 to 80 µm and, as a powder, a loose bulk density of 0.35 to 0.60.

Seventh, an excipient for compressed tablets according to the above first or sixth, characterized in that it comprises spherical particles of crystalline mannitol having a mean diameter of 20 to 80 µm and, as a powder, an angle of repose of 30 to 50 degrees.

Eighth, an excipient for compressed tablets according to any one of the above first to seventh, characterized in that it comprises spherical particles of crystalline mannitol made by spray drying, Ninth, a tablet made with excipients for compressed tablets according to any one of the above first to eighth.

Tenth, a tablet according to the above ninth, made with 100 parts by weight of spherical particles of crystalline mannitol and 0.5 parts by weight of magnesium stearate as a lubricating and glossing agent, under a compressing force of 800 kgf to have a tablet hardness of 7.0 to 11.0 kgf and a tablet disintegrating time of 0.05 to 2.5 minutes.

Eleventh, a tablet according to the above ninth, made with 95 parts by weight of spherical particles of crystalline mannitol, 5 parts by weight of low-substitution hydroxypropyl cellulose as a disintegrating agent and 0.5 parts by weight of magnesium stearate as a lubricating and glossing agent, under a compressing force of 800 kgf to have a tablet hardness of 7.5 to 13.0 kgf and a tablet disintegrating time of 0.05 to 0.7 minutes.

Twelfth, a tablet according to the above ninth, made with 95 parts by weight of spherical particles of crystalline mannitol, 5 parts by weight of carmellose calcium as a disintegrating agent and 0.5 parts by weight of magnesium stearate as a lubricating and glossing agent, under a compressing force of 800 kgf to have a tablet hardness of 6.0 to 12.0 kgf and a tablet disintegrating time of 0.05 to 0.7 minutes.

Thirteenth, a tablet according to the above ninth, made with 55.3 parts by weight of spherical particles of crystalline mannitol, 1 part by weight of ascorbic acid, 23.7 parts by weight of corn starch, 20 parts by weight of crystalline cellulose and 0.5 parts by weight of magnesium stearate as a lubricating and glossing agent, under a compressing force of 800 kgf to have a tablet hardness of 5.0 to 10.0 kgf.

Fourteenth, a tablet according to the above ninth, made with 96.0 parts by weight of spherical particles of crystalline mannitol, 3.5 parts by weight of solid content in 10% hydroxypropyl cellulose aqueous solution, mixed, granulated, dried in a fluidized bed granulator, 100 parts by weight of granules thus obtained and 0.5 parts by weight of magnesium stearate as a lubricating and glossing agent, under a compressing force of 800 kgf to have a tablet hardness of 8.0 to 16.0 kgf and a tablet disintegrating time of 0.05 to 9.0 minutes.

Fifteenth, a tablet according to the above ninth, made with 66.5 parts by weight of spherical particles of crystalline mannitol, 1 part by weight of ascorbic acid, 28.5 parts by weight of corn starch, 3.5 parts by weight of solid content in 10% hydroxypropyl cellulose aqueous solution, mixed, granulated, dried in a fluidized bed granulator, 100 parts by weight of granules thus obtained and 0.5 parts by weight of magnesium stearate as a lubricating and glossing agent, under a compressing force of 800 kgf to have a tablet hardness of 7.0 to 12.0 kgf.

Sixteenth, an excipient for compressed tablets according to the above first, characterized in that it comprises spherical particles of crystalline mannitol having a mean diameter of 15 to 100 μm and, as a powder, a loose bulk density of 0.35 to 0.60 and/or an angle of repose of 30 to 50 degrees.

Seventeenth, an excipient for compressed tablets according to the above first, characterized in that it comprises spherical particles of crystalline mannitol having a mean diameter of 15 to 85 μm and, as a powder, a loose bulk density of 0.35 to 0.60 and/or an angle of repose of 30 to 50 degrees.

Eighteenth, an excipient for compressed tablets according to the above first, characterized in that it comprises spherical particles of crystalline mannitol having a mean diameter of 20 to 80 μm and, as a powder, a loose bulk density of 0.35 to 0.60 and/or an angle of repose of 30 to 50 degrees.

Nineteenth, an excipient for compressed tablets according to any one of the above first to eighth and sixteenth to eighteenth, characterized in that at least 30% of the spherical particles of crystalline mannitol have a diameter smaller than 74 μm.

Twentieth, a tablet made with an excipient for compressed tablets according to any one of the above sixteenth to nineteenth.

Twenty-first, a tablet according to the above twentieth, made with 100 parts by weight of spherical particles of crystalline mannitol and 0.5 parts by weight of magnesium stearate as a lubricating and glossing agent, under a compressing force of 800 kgf to have a tablet hardness of 7.0 to 11.0 kgf and a tablet disintegrating time of 0.05 to 2.5 minutes.

Twenty-second, a tablet according to the above twentieth, made with 95 parts by weight of spherical particles of crystalline mannitol, 5 parts by weight of low-substitution hydroxypropyl cellulose as a disintegrating agent and 0.5 parts by weight of magnesium stearate as a lubricating and glossing agent, under a compressing force of 800 kgf to have a tablet hardness of 7.5 to 13.0 kgf and a tablet disintegrating time of 0.05 to 0.7 minutes.

Twenty-third, a tablet according to the above twentieth, made with 95 parts by weight of spherical particles of crystalline mannitol, 5 parts by weight of carmellose calcium as a disintegrating agent and 0.5 parts by weight of magnesium stearate as a lubricating and glossing agent, under a compressing force of 800 kgf to have a tablet hardness of 6.0 to 12.0 kgf and a tablet disintegrating time of 0.05 to 0.7 minutes.

Twenty-fourth, a tablet according to the above twentieth, made with 55.3 parts by weight of spherical particles of crystalline mannitol, 1 part by weight of ascorbic acid, 23.7 parts by weight of corn starch, 20 parts by weight of crystalline cellulose and 0.5 parts by weight of magnesium stearate as a lubricating and glossing agent, under a compressing force of 800 kgf to have a tablet hardness of 5.0 to 10.0 kgf.

Twenty-fifth, a tablet according to the above twentieth, made with 96.0 parts by weight of spherical particles of crystalline mannitol, 3.5 parts by weight of solid content in 10% hydroxypropyl cellulose aqueous solution, mixed, granulated, dried in a fluidized bed granulator, 100 parts by weight of granules thus obtained and 0.5 parts by weight of magnesium stearate as a lubricating and glossing agent, under a compressing force of 800 kgf to have a tablet hardness of 8.0 to 16.0 kgf and a tablet disintegrating time of 0.05 to 9.0 minutes.

Twenty-sixth, a tablet according to the above twentieth, made with 66.5 parts by weight of spherical particles of crystalline mannitol, 1 part by weight of ascorbic acid, 28.5 parts by weight of corn starch, 3.5 parts by weight of solid content in 10% hydroxypropyl cellulose aqueous solution, mixed, granulated, dried in a fluidized bed granulator, 100 parts by weight of granules thus obtained and 0.5 parts by weight of magnesium stearate as a lubricating and glossing agent, under a compressing force of 800 kgf to have a tablet hardness of 7.0 to 12.0 kgf.

Thanks to the excipient for compressed tablets of the present invention, spherical particles of crystalline mannitol obtained by spray drying can be used directly for compressing, as they are, while utilizable also for indirect compressing, as granulated with other ingredients.

When making tablets with the excipient for compressed tablets of the present invention, any ingredients usually used for tablets can be used as combined with the excipient for compressed tablets of the present invention, without limitation.

Disintegrating agents to be mentioned are e.g. starches like corn starch, potato starch, rice starch, pregelatinized starch, carmellose calcium, croscarmellose sodium, carmellose, carmellose sodium, sodium carboxymethyl starch, crospovidone, low-substituted hydroxypropyl cellulose, hydroxypropyl cellulose. These disintegrating agents can be used singly or in mixture of two or more of them together at an appropriate mixing ratio.

Lubricating and glossing agents to be mentioned are e.g. magnesium stearate, calcium stearate, stearyl sodium fumarate, sucrose fatty acid ester, polyethylene glycol, talc, stearic acid, etc.

Binders to be mentioned are e.g. hydroxypropyl cellulose, hydroxypropyl methyl cellulose, crystalline cellulose, pregelatinized starch, polyvinyl pyrolydon, gum arabic powder, gelatin, pullulan. These binders can be used, in mixture of two or more of them at any mixing ratio as needed.

In the present invention, another excipient can be used in combination with the excipient of the present invention, when further needed. Organic excipients utilizable in such a case are saccharides like xylose, mannose, glucose, maltose, isomaltose, maltotriose, dextrin, starch hydrolysate, sugar alcohols like xylitol, sorbitol, maltitol, isomaltitol, maltotriitol, reduced dextrin, hydrogenated starch hydrolysate, while spherical particles of crystalline mannitol can be used with other mannitol like crystallized or pulverized ones for the purpose of adjusting the hardness, disintegrating time, etc.

Then, inorganic excipients to be mentioned are e.g. calcium phosphate anhydrate, precipitated calcium carbonate, calcium silicate, light anhydrous silicic acid. These excipients can be used in mixture of two or more of them, regardless of whether they are organic or inorganic.

Medicinal ingredients used in the present invention can be solid, powder, crystalline, oily, solution or in any other form but one, two or more selected from a group of nutritious or alimentary health supplement, antipyretic analgesic antiphlogistic, psychotropic, antianxiety drug, antidepressant, hypnotic, anticonvulsant, analeptic, brain metabolism improver, brain circulation improver, antiepileptic, oxymetazoline, digestant, antacid, antiulcer drug, antitussive-expectorant, antiemetic, respiratory stimulant, bronchia dilator, antiallergenic, dental drug, antihistamine, cardiant, antiarrythmic, diuretic, blood pressure-lowering drug, blood vessels shrinker, coronary blood vessels dilator, peripheral blood vessels dilator, anti-hyperlipemia drug, cholagogue, antibiotic, chemotherapy drug, antidiabetic, anti-osteoporosis drug, antirheumatic, skeletal muscles relaxant, antispastic, hormone supplement, alkaloidal drug, sulfa drug, anti-gout drug, anticoagulant, anti-anaplastic tumor drug, anti-Alzheimer's disease drug. Then, nutritious or alimentary health supplement, antipyretic analgesic antiphlogistic, hypnotic, analeptic, digestant, antiulcer drug, antitussive-expectorant, anti-allergenic, antiarrythmic, diuretic, blood pressure-lowering drug, blood vessels shrinker, coronary blood vessels dilator, anti-hyperlipemia drug, antidiabetic, anti-osteoporosis drug, skeletal muscles relaxant, motion sickness relief in particular are advantageously used.

As used here in the present invention, the term "aspect ratio" refers to a ratio of the major axis to the minor axis of the particle, which is an index of the sphericity. This major axis/minor axis ratio is determined by photographing the test piece particles with a scanning electron microscope (S-2600N, manufactured by Hitachi, Ltd.), without vapor deposition, at an acceleration voltage of 20 kV, in a vacuum of 50 Pa, under a magnification of ×1500 to measure respectively the length of the major axis (i.e., longer diameter) and the length of the minor axis (i.e., shorter diameter) taken vertical to the major axis at the midpoint for 30 particles, calculating the ratio of the longer diameter to the shorter diameter for each particle, and then averaging the determined values for the 30 particles.

As used here in the present invention, the term "oil absorption rate according to Test A" is explained as follows. 30 g of medium-chain fatty acid triglyceride (COCONAD MT, manufactured by KAO Corporation) and 15 g of sample mannitol are put into a glass beaker having a capacity of 100 mL to mix with spatula the oil and the sample powder gently enough to avoid crushing the fine particles, followed by transferring them into a vacuum constant temperature dryer (VOS-300D, manufactured by EYELA) for oil impregnation at room temperature under a reduced pressure of 0.67 Pa for three hours.

Then, it is transferred into a centrifuge tube having bottom holes, with a filtering cloth having openings of 45 μm (325 mesh) spread inside to undergo centrifugal separation with a centrifugal separator (H-500R, manufactured by KOKUSAN K.K.) under a pressure of about 1300 G for 10 minutes. After centrifugal separation, the weight of the test piece remaining in the centrifuge tube (weight a) is obtained from the weight of the centrifuge tube with the test piece and the tare weight of the centrifuge tube. Then, the value calculated by the following equation 1 is named "oil absorption rate 1".

$$\text{Oil absorption rate } 1(\%) = [(\text{weight } a - 15)/15] \times 100 \quad \text{(Equation 1)}$$

Then, the centrifuge tube containing the test piece after centrifugal separation is placed in a glass beaker of 100 mL, followed by addition of 20 g of n-hexane over the test piece powder to undergo centrifugal separation with a centrifugal separator under a pressure of about 1300 G for 10 minutes. After centrifugal separation, the weight of the test piece remaining in the centrifuge tube (weight b) is obtained from the weight of the centrifuge tube with the test piece and the tare weight of the centrifuge tube. Then, the value calculated by the following equation 2 is named "oil absorption rate 2".

$$\text{Oil absorption rate } 2(\%) = [(\text{weight } b - 15)/15] \times 100 \quad \text{(Equation 2)}$$

As used here in the present invention, the term "mean particle diameter" refers to what is called "median diameter" in general i.e. a particle diameter giving 50% of fine particles integration distribution.

To measure the mean particle diameter, Laser Diffraction Particle Size Analyzer MT-3000 (manufactured by Nikkiso Co., Ltd.) and 2-propanol (first class grade chemical having a purity of 99.0% or more, manufactured by Wako Pure Chemical Industries, Ltd.) as a dispersant solvent are used. Addition of the test piece is continued till the display indicates "right amount", and it is put under ultrasonic treatment for 30 seconds with an ultrasonic output of 40 W, and then, the mean particle diameter is measured. The above steps are repeated twice for one type of test piece and the mean value thus obtained will be named "mean particle diameter".

As used here in the present invention, the term "loose bulk density" refers to a filling density of a powder after a free fall into a predetermined container that will be determined with an A.B.D. Powder Tester (manufactured by TSUTSUI SCIENTIFIC INSTRUMENTS CO., LTD.) as follows.

A test piece container (having a capacity of 100 mL) is placed on a round measurement bench. Then, the test piece is dropped from the test piece hopper, with the ejection nozzle removed, into the test piece container till the test piece is heaped up. The top of the heap is leveled off with a leveling spatula to measure the weight. The same steps are repeated three times for one type of test piece to obtain the mean value that is a loose bulk density.

As used here in the present invention, the term "angle of repose" refers to an angle of a slope of a pile formed when a powder is poured onto a circular plate by a free fall drop, determined by A.B.D. Powder Tester (manufactured by TSUTSUI SCIENTIFIC INSTRUMENTS CO., LTD.) as follows. A test piece charged into a test piece hopper is dropped onto a circular plate of an angle of repose test piece bench through a vibrating bar, net (having openings of 1000 μm), ejection funnel and nozzle (having an inner diameter of 1 cm). Then, the angle of the slope is measured with an angle meter at three different spots different in direction. The same steps are repeated three times to obtain the mean value i.e. the angle of repose.

As used here in the present invention, the term "tablet hardness" refers to a mean value obtained by measuring the tablet hardness of 10 pieces of each test piece by a tablet hardness meter (TH-203CP, manufactured by Toyama Sangyo Co., Ltd.).

As used here in the present invention, the term "tablet disintegration time" refers to a value measured by two methods that will be explained later. As used here in the present invention, the term "tablet disintegration time (1)" refers to a mean value obtained after measuring the time needed for 6 pieces of each test piece to disintegrate at a water temperature of 37° C. by a tablet disintegration tester (NT-2H, manufactured by Toyama Sangyo Co., Ltd.) in conformity with Amendment 15 of the Pharmacopoeia of Japan. As used here in the present invention, the term "tablet disintegration time (2)" refers to a measured value of time needed for a tablet of the present invention placed within a healthy adult's mouth without water to be completely disintegrated and dissolved only with saliva.

More detailed and specific conditions will be explained, referring to Examples.

ADVANTAGEOUS EFFECTS OF THE INVENTION

Thanks to the use of the excipient for compressed tablets of the present invention, the conventional problem of a failure to make a tablet excellent in all of tablet hardness, stability under high humidity condition, chemical stability of active components and disintegration in mouth has been overcome.

More particularly, thanks to the formula in which spherical particles of crystalline mannitol are used as an excipient for medicinal preparations with addition of a disintegrating agent according to the present invention, ideally disintegrating tablets excellent in tablet hardness and better in tablet disintegration than using direct compressing mannitol conventionally on the market have been obtained.

Moreover, when granulates made of spherical particles of crystalline mannitol and active components are processed into tablets, higher hardness is obtained than using lactose and commercially available mannitol, thereby overcoming the conventional problems.

In addition, thanks to the very specific structure of the spherical particles of crystalline mannitol used in the present invention, extremely spherical and internally cavitary, particles have many contacts with one another to bind one another strongly when processed into tablets, while the solvent is quickly introduced into the cavities inside the particles, enabling earlier disintegration of the tablets.

On the other hand, also in the case of granulation of spherical particles of crystalline mannitol and active components, the spherical particles of crystalline mannitol keep their shape even within granulates as observed by an electron microscopic photography, obviously unlike the shape of commercial products. Therefore, the spherical particles of crystalline mannitol keep their characteristics even when granulated.

BRIEF EXPLANATION OF THE DRAWINGS

FIG. 1 Graphical presentation of tablet hardness and tablet disintegration time (2) of the actual examples of the present invention and the controls.

FIG. 2 Graphical presentation of tablet hardness and tablet disintegration time (2) of the actual examples of the present invention and the controls.

MODE OF CARRYING OUT THE INVENTION

The mannitol excipient of the present invention will be explained here below, also referring to Examples that will not limit the technical scope of the present invention.
(Spray Dryer Used in Making Spherical Particles of Crystalline Mannitol)

Spray dryer ODT-20 (manufactured by Ohkawara Kakohki Co., Ltd.) was used to make test pieces. An atomizer was installed, with a product collecting can placed under itself and the M pin-type disk (having a disk diameter of 84 mmφ, manufactured by Ohkawara Kakohki Co., Ltd.) above itself, introducing mannitol aqueous solution into the atomizer through a pair of Teflon (registered trademark) tubes (having an outer diameter of 6 mm and inner diameter of 4 mmφ). Hot air was introduced from the upper part, under a concurrent flow system in which air is jetted in the same direction with respect to sprayed liquid to form a whirlpool current, and was ejected from the lower part.
(Spherical Particles of Crystalline Mannitol 1 Used in Examples: Raw Material 1)

20 parts by weight of commercially available crystalline product (Mannit P, manufactured by Mitsubishi Shoji Foodtech Co., Ltd.) as mannitol and in addition, 80 parts by weight of pure water are heated together till complete dissolution of solid ingredients to obtain a clear solution. Then, mannitol aqueous solution at a temperature of 70° C. having a solid content of 20%, thus obtained, was used for spray drying.

The atomizer was set at a rotational speed of 25000 rpm, hot air was introduced into the spray dryer at a temperature of 100° C. at the inlet and the amount of the introduced hot air was 7 m$^3$/min. Then, 20% mannitol aqueous solution was introduced at a rate of 6.5 kg/hr. After introduction of 30 kg of mannitol aqueous solution prepared beforehand, powder stored in the can under the spray dryer was collected and dried with a fluidized-bed dryer (FLO-5, manufactured by OKAWARA MFG. CO., LTD.) at a temperature of 80° C. for ten minutes, thereby obtaining spherical particles of crystalline mannitol (raw material 1) to be used in Examples. These particles had a mean diameter of 25 μm.
(Spherical Particles of Crystalline Mannitol 2 Used in Examples: Raw Material 2)

20 parts by weight of commercially available crystalline product (Mannit P, manufactured by Mitsubishi Shoji Foodtech Co., Ltd.) as mannitol and in addition, 80 parts by weight of pure water were heated together till complete dissolution of solid ingredients to obtain a clear solution. Then, mannitol aqueous solution at a temperature of 70° C. having a solid content of 20%, thus obtained, was used for spray drying.

The atomizer was set at a rotational speed of 15000 rpm, hot air was introduced into the spray dryer at a temperature of 100° C. at the inlet and the amount of the introduced hot air was 7 m$^3$/min. Then, 20% mannitol aqueous solution was introduced at a rate of 6.5 kg/hr. After introduction of 30 kg of mannitol aqueous solution prepared beforehand, powder stored in the can under the spray dryer was collected and dried with a fluidized-bed dryer (FLO-5, manufactured by OKAWARA MFG. CO., LTD.) at a temperature of 80° C. for ten minutes, thereby obtaining spherical particles of crystalline mannitol (raw material 2) to be used in Examples. These particles had a mean diameter of 44 μm.
(Spherical Particles of Crystalline Mannitol 3 Used in Examples: Raw Material 3)

15 parts by weight of commercially available crystalline product (Mannit P, manufactured by Mitsubishi Shoji Foodtech Co., Ltd.) as mannitol and in addition, 85 parts by weight of pure water were heated together till complete dissolution of solid ingredients to obtain a clear solution. Then, mannitol aqueous solution at a temperature of 70° C. having a solid content of 15%, thus obtained, was used for spray drying.

The atomizer was set at a rotational speed of 8500 rpm, hot air was introduced into the spray dryer at a temperature of 150° C. at the inlet and the amount of the introduced hot air was 7 m$^3$/min. Then, 15% mannitol aqueous solution was introduced at a rate of 6.5 kg/hr. After introduction of 30 kg of mannitol aqueous solution prepared beforehand, powder stored in the can under the spray dryer was collected and dried with a fluidized-bed dryer (FLO-5, manufactured by OKAWARA MFG, CO., LTD.) at a temperature of 80° C. for ten minutes, thereby obtaining spherical particles of crystalline mannitol to be used in Examples. These particles had a mean diameter of 60 μm.

(Spherical Particles of Crystalline Mannitol 4 Used in Examples: Raw Material 4)

20 parts by weight of commercially available crystalline product (Mannit P, manufactured by Mitsubishi Shoji Foodtech Co., Ltd.) as mannitol and in addition, 80 parts by weight of pure water were heated together till complete dissolution of solid ingredients to obtain a clear solution. Then, mannitol aqueous solution at a temperature of 70° C. having a solid content of 20%, thus obtained, was used for spray drying, The atomizer was set at a rotational speed of 7000 rpm, hot air was introduced into the spray dryer at a temperature of 100° C. at the inlet and the amount of the introduced hot air was 7 m$^3$/min. Then, 20% mannitol aqueous solution was introduced at a rate of 6.5 kg/hr. After introduction of 30 kg of mannitol aqueous solution prepared beforehand, powder stored in the can under the spray dryer was collected and dried with a fluidized-bed dryer (FLO-5, manufactured by OKAWARA MFG. CO., LTD.) at a temperature of 80° C. for ten minutes, thereby obtaining spherical particles of crystalline mannitol (raw material 4) to be used in Examples. These particles had a mean diameter of 76 μm.

Physical and chemical properties of such raw materials used in the Examples and manufacturing conditions are shown in Table 1.

TABLE 1

Mean particle diameter, loose bulk density, angle of repose, aspect ratio, oil absorption rate and manufacturing conditions of raw materials used in Examples

|  | Raw material 1 | Raw material 2 | Raw material 3 | Raw material 4 |
| --- | --- | --- | --- | --- |
| Mean particle diameter (μm) | 25 | 44 | 60 | 76 |
| Loose bulk density | 0.47 | 0.48 | 0.40 | 0.45 |
| Angle of repose (°) | 44 | 39 | 39 | 36 |
| Aspect ratio | 1.0 | 1.0 | 1.0 | 1.1 |
| Oil absorption rate 1 (%) | 40.7 | 31.0 | 50.9 | 53.9 |
| Oil absorption rate 2 (%) | 23.9 | 20.1 | 29.8 | 34.4 |
| Atomizer's rotational speed (rpm) | 25000 | 15000 | 8500 | 7000 |
| Inlet temperature (° C.) | 100 | 100 | 150 | 100 |
| Ventilation (m$^3$/min.) | 7 | 7 | 7 | 7 |
| Liquid supply (kg/h) | 6.5 | 6.5 | 6.5 | 6.5 |
| Spray liquid concentration (%) | 20 | 20 | 15 | 20 |
| Spray liquid temperature (° C.) | 70 | 70 | 70 | 70 |

(Compressing Machine Used in the Examples and Comparative Examples)

Powders were processed into tablets in the Examples and Comparative Examples by a VIRGO 0512SS2AZ compressing machine, manufactured by KIKUSUI SEISAKUSHO LTD.

(Commercial Products for Comparative Examples)

Mannitol and lactose as commercial products used for Comparative Examples were the following.

Commercially Available Mannitol

Commercial product 1: Mannit P, manufactured by Mitsubishi Shoji Foodtech Co., Ltd.

Commercial product 2: Pearlitol 100SD, manufactured by ROQUETTE FRERES

Commercial product 3: Pearlitol 200SD, manufactured by ROQUETTE FRERES

Commercial product 4: Parteck M200, manufactured by Merck

Commercially Available Lactose

Commercial product 5: Pharmatose DCL-11, manufactured by DMV

Commercial product 6: Dilactose-S, manufactured by Freund Industrial, Co., Ltd.

Commercial product 7: Lactose 200M, manufactured by DMV

Example 1

Single Formula, Direct Compressing 100 parts by weight of spherical particles of crystalline mannitol and in addition, 0.6 parts by weight of magnesium stearate (manufactured by Wako Pure Chemical Industries) as a lubricating and glossing agent were processed into tablets, with tablet molds of 8 mm flat, unit weight of 180 mg, single pounder, as measured, at a rotational speed of 30 rpm, under a compressing force of 800 kgf.

The values of tablet hardness and tablet disintegration time (1) about thus obtained products according to the present invention (hereinafter, "actual examples") 1-1 to 1-4 are shown in Table 2.

TABLE 2

Tablet hardness and tablet disintegration time (1) of actual examples 1-1 to 1-4, and controls 1-1 and 1-5 to 1-7

| (Single formula, direct compressing) | Excipient | Tablet hardness (kgf) | Tablet disintegration time (1) (min.) |
| --- | --- | --- | --- |
| Actual example 1-1 | Raw material 1 | 9.4 | 1.5 |
| Actual example 1-2 | Raw material 2 | 10.2 | 1.4 |
| Actual example 1-3 | Raw material 3 | 7.6 | 2.0 |
| Actual example 1-4 | Raw material 4 | 7.4 | 1.6 |
| Control 1-1 | Mannit P | 2.5 | 5.7 |
| Control 1-5 | Pharmatose | 3.9 | 11.8 |
| Control 1-6 | Dilactose-S | 5.4 | 5.9 |
| Control 1-7 | Lactose 200M | 3.7 | 1.8 |

Comparative Example 1

Single Formula, Direct Compressing

The same method as in Example 1 was used to make tablets, except for the use of commercial products 1, 5 to 7, instead of spherical particles of crystalline mannitol used in Example 1.

The values of tablet hardness and tablet disintegration time (1) about thus obtained products for the comparison (hereinafter, "controls") 1-1, 1-5 to 1-7 are shown in Table 2.

In the form of tablets made of only excipients, the actual examples of the present invention have proved harder and quicker to disintegrate than the controls in general, thereby achieving the compatibility of high hardness and quick disintegration.

Example 2

Disintegrating Agent Addition Formula-1, Direct Compressing 95 parts by weight of spherical particles of crystalline mannitol and in addition, 5 parts by weight of low-substituted hydroxypropyl cellulose (L-HPC LH-11, manufactured by Shin-Etsu Chemical Co., Ltd.) as a disintegrating agent and 0.5 parts by weight of magnesium stearate (manufactured by Wako Pure Chemical Industries, Ltd.) as a lubricating and glossing agent were processed into tablets, with tablet molds of 8 mm flat, unit weight of 180 mg, single pounder, as measured, at a rotational speed of 30 rpm, under a compressing force of 800 kgf, The values of tablet hardness and tablet disintegration time (1) about thus obtained actual examples 2-1 to 2-4 are shown in Table 3.

TABLE 3

Tablet hardness and tablet disintegration time (1) of actual examples 2-1 to 2-4, and control 2-1

| (Disintegrating agent addition formula-1, direct compressing) | Excipient | Tablet hardness (kgf) | Tablet disintegration time (1) (min.) |
|---|---|---|---|
| Actual example 2-1 | Raw material 1 | 12.6 | 0.6 |
| Actual example 2-2 | Raw material 2 | 10.7 | 0.4 |
| Actual example 2-3 | Raw material 3 | 7.9 | 0.3 |
| Actual example 2-4 | Raw material 4 | 7.8 | 0.3 |
| Control 2-1 | Mannit P | 1.5 | 0.2 |

Comparative Example 2

Disintegrating Agent Addition Formula-1, Direct Compressing

The same method as in Example 2 was used to make tablets, except for the use of commercial product 1 instead of spherical particles of crystalline mannitol used in Example 2.

The values of tablet hardness and tablet disintegration time (1) about thus obtained control 2-1 are shown in Table 3.

The actual examples of the present invention have proved excellent in tablet hardness and quicker in terms of disintegration time as well, while the control showed hardness that could have no practicability.

Example 3

Disintegrating Agent Addition Formula-2, Direct Compressing

The same method as in Example 2 was used to make tablets, except for the use of carmellose calcium (CMC-Ca ECG-FA, manufactured by NICHIRIN CHEMICAL INDUSTRIES, LTD.) as a disintegrating agent.

The values of tablet hardness and tablet disintegration time (1) about thus obtained actual examples 3-1 to 3-4 are shown in Table 4.

TABLE 4

Tablet hardness and tablet disintegration time (1) of actual examples 3-1 to 3-4, and control 3-1

| (Disintegrating agent addition formula-2, direct compressing) | Excipient | Tablet hardness (kgf) | Tablet disintegration time (1) (min.) |
|---|---|---|---|
| Actual example 3-1 | Raw material 1 | 11.1 | 0.7 |
| Actual example 3-2 | Raw material 2 | 11.8 | 0.5 |
| Actual example 3-3 | Raw material 3 | 7.2 | 0.6 |
| Actual example 3-4 | Raw material 4 | 6.7 | 0.7 |
| Control 3-1 | Mannit P | 1.1 | 0.3 |

Comparative Example 3

Disintegrating Agent Addition Formula-2, Direct Compressing

The same method as in Example 3 was used to make tablets, except for the use of commercial product 1 instead of spherical particles of crystalline mannitol used in Example 3, The values of tablet hardness and tablet disintegration time (1) about thus obtained control 3-1 are shown in Table 4.

The actual examples of the present invention have proved excellent in tablet hardness and quicker in terms of disintegration time as well, while the control showed hardness that could have no practicability.

Example 4

Disintegrating Agent Addition Formula-3, Direct Compressing 99 parts by weight of spherical particles of crystalline mannitol and in addition, 1 part by weight of low-substituted hydroxypropyl cellulose (L-HPC LH-11, manufactured by Shin-Etsu Chemical Co., Ltd.) as a disintegrating agent and 0.5 parts by weight of magnesium stearate (manufactured by Wako Pure Chemical Industries, Ltd.) as a lubricating and glossing agent were processed into tablets, with tablet molds of 8 mm flat, unit weight of 180 mg, single pounder, as measured, at a rotational speed of 30 rpm, under a compressing force of 800 kgf.

The values of tablet hardness and tablet disintegration time (2) about thus obtained actual examples 4-1 to 4-4 are shown in Table 5.

TABLE 5

Tablet hardness and tablet disintegration time (2) of actual examples 4-1 to 4-4, and controls 4-1 to 4-4

| (Disintegrating agent addition formula-3, direct compressing) | Excipient | Tablet hardness (kgf) | Tablet disintegration time (2) (sec.) |
|---|---|---|---|
| Actual example 4-1 | Raw material 1 | 7.7 | 62 |
| Actual example 4-2 | Raw material 2 | 9.5 | 41 |
| Actual example 4-3 | Raw material 3 | 9.3 | 48 |
| Actual example 4-4 | Raw material 4 | 8.1 | 47 |
| Control 4-1 | Mannit P | 3.2 | 17 |
| Control 4-2 | Pearlitol 100SD | 9.4 | 102 |
| Control 4-3 | Pearlitol 200SD | 9.2 | 84 |
| Control 4-4 | Parteck M200 | 13.0 | 104 |

Comparative Example 4

Disintegrating Agent Addition Formula-3, Direct Compressing

The same method as in Example 4 was used to make tablets, except for the use of commercial products 1 to 4 instead of spherical particles of crystalline mannitol used in Example 4.

The values of tablet hardness and tablet disintegration time (2) about thus obtained controls 4-1 to 4-4 are shown in Table 5.

The actual examples have proved itself a good disintegrating agent, while control 4-1 showed hardness that could have no practicability and controls 4-2 to 4-4 were as hard as the actual examples but much slower to disintegrate, degraded in performance as a disintegrating agent.

Example 5

Disintegrating Agent Addition Formula-4, Direct Compressing

The same method as in Example 4 was used to make tablets, except for the use of crospovidone (Kollidon CL-SF, manufactured by BASF Japan) as a disintegrating agent The values of tablet hardness and tablet disintegration time (2) about thus obtained actual examples 5-1 to 5-4 are shown in Table 6.

TABLE 6

Tablet hardness and tablet disintegration time (2) of actual examples 5-1 to 5-4, and controls 5-1 to 5-4

| | Excipient | Tablet hardness (kgf) | Tablet disintegration time (2) (sec.) |
|---|---|---|---|
| Actual example 5-1 | Raw material 1 | 7.5 | 27 |
| Actual example 5-2 | Raw material 2 | 10.1 | 33 |
| Actual example 5-3 | Raw material 3 | 8.6 | 32 |
| Actual example 5-4 | Raw material 4 | 7.8 | 35 |
| Control 5-1 | Mannit P | 1.8 | 19 |
| Control 5-2 | Pearlitol 100SD | 9.8 | 103 |
| Control 5-3 | Pearlitol 200SD | 9.0 | 80 |
| Control 5-4 | Parteck M200 | 12.6 | 101 |

Comparative Example 5

Disintegrating Agent Addition Formula-4, Direct Compressing

The same method as in Example 5 was used to make tablets, except for the use of commercial products 1 to 4 instead of spherical particles of crystalline mannitol used in Example 5.

The values of tablet hardness and tablet disintegration time (2) about thus obtained controls 5-1 to 5-4 are shown in Table 6.

The actual examples have proved itself a good disintegrating agent, while control 5-1 showed hardness that could have no practicability and controls 5-2 to 5-4 were as hard as the actual examples but much slower to disintegrate, degraded in performance as a disintegrating agent.

Example 6

Disintegrating Agent Addition Formula-5, Direct Compressing

The same method as in Example 2 was used to make tablets, except for the use of crospovidone (Kollidon CL-SF, manufactured by BASF Japan) as a disintegrating agent.

The values of tablet hardness and tablet disintegration time (2) about thus obtained actual examples 6-1 to 6-4 are shown in Table 7.

TABLE 7

Tablet hardness and tablet disintegration time (2) of actual examples 6-1 to 6-4, and controls 6-1 to 6-4

| | Excipient | Tablet hardness (kgf) | Tablet disintegration time (2) (sec.) |
|---|---|---|---|
| Actual example 6-1 | Raw material 1 | 8.1 | 18 |
| Actual example 6-2 | Raw material 2 | 10.1 | 19 |
| Actual example 6-3 | Raw material 3 | 8.1 | 18 |
| Actual example 6-4 | Raw material 4 | 7.6 | 20 |
| Control 6-1 | Mannit P | 1.8 | 19 |
| Control 6-2 | Pearlitol 100SD | 8.8 | 45 |

TABLE 7-continued

Tablet hardness and tablet disintegration time (2) of actual examples 6-1 to 6-4, and controls 6-1 to 6-4

|  | Excipient | Tablet hardness (kgf) | Tablet disintegration time (2) (sec.) |
|---|---|---|---|
| Control 6-3 | Pearlitol 200SD | 8.8 | 36 |
| Control 6-4 | Parteck M200 | 13.7 | 60 |

Comparative Example 6

Disintegrating Agent Addition Formula-5, Direct Compressing

The same method as in Example 6 was used to make tablets, except for the use of commercial products 1 to 4 instead of spherical particles of crystalline mannitol used in Example 6.

The values of tablet hardness and tablet disintegration time (2) about thus obtained controls 6-1 to 6-4 as shown in Table 7.

The actual examples have proved itself a good disintegrating agent, while control 6-1 showed hardness that could have no practicability and controls 6-2 to 6-4 were as hard as the actual examples but much slower to disintegrate, degraded in performance as a disintegrating agent.

Example 7

Standard Formula, Direct Compressing 55.3 parts by weight of spherical particles of crystalline mannitol passing through a sieve having openings of 500 μm, 1 part by weight of ascorbic acid (100 M ascorbic acid, manufactured by BASF) passing through a sieve having openings of 500 μm, 23.7 parts by weight of corn starch (corn starch, manufactured by NIHON SHOKUHIN KAKO CO., LTD) passing through a sieve having openings of 500 μm and 20 parts by weight of crystalline cellulose (CEOLUS PH101, manufactured by Asahi Kasei Chemicals Corporation) were mixed in a V-type mixer (TRANSPARENT MICRO MIXER, manufactured by TSUTSUI SCIENTIFIC INSTRUMENTS CO., LTD.) for thirty minutes, and further mixed with 0.5 parts by weight of magnesium stearate (manufactured by Wako Pure Chemical Industries, Ltd.) having passed through a sieve having openings of 500 μm in addition for 5 minutes. This powder thus obtained was processed into tablets with tablet molds of 8 mm flat, unit weight of 180 mg, single pounder, continuously, at a rotational speed of 30 rpm, under a compressing force of 800 kgf.

The values of tablet hardness about thus obtained actual examples 7-1 to 7-4 are shown in Table 8.

TABLE 8

Tablet hardness of actual examples 7-1 to 7-4, and controls 7-1 and 7-5

| (Standard formula, direct compressing) | Excipient | Tablet hardness (kgf) |
|---|---|---|
| Actual example 7-1 | Raw material 1 | 9.6 |
| Actual example 7-2 | Raw material 2 | 7.2 |
| Actual example 7-3 | Raw material 3 | 5.6 |
| Actual example 7-4 | Raw material 4 | 5.1 |
| Control 7-1 | Mannit P | 4.3 |
| Control 7-5 | Pharmatose | 2.8 |

Comparative Example 7

Standard Formula, Direct Compressing

The same method was used to make tablets as in Example 7, except for the use of commercial products 1 and 5 instead of spherical particles of crystalline mannitol used in Example 7.

The values of tablet hardness about thus obtained controls 7-1 and 7-5 are shown in Table 8.

The actual examples have proved harder than the control.

Example 8

Single Formula, Granulation 96.0 parts by weight of spherical particles of crystalline mannitol passing through a sieve having openings of 500 μm, and 35.0 parts by weight of 10% aqueous solution of hydroxypropyl cellulose (HPC-L, manufactured by Nippon Soda Co., Ltd.) passing through a sieve having openings of 500 μm (3.5 parts by weight of hydroxypropyl cellulose on a solid basis) were mixed, granulated and dried in a fluidized-bed granulator (FLO-MINI, manufactured by OKAWARA MFG. CO., LTD.).

100 parts by weight of granulates thus obtained and, in addition, 0.5 parts by weight of magnesium stearate (manufactured by Wako Pure Chemical Industries, Ltd.) as a lubricating and glossing agent were processed into tablets, with tablet molds of 8 mm flat, unit weight of 180 mg, single pounder, as measured, at a rotational speed of 30 rpm, under a compressing force of 800 kgf.

The values of tablet hardness and tablet disintegration time (1) about thus obtained actual examples 8-1 to 8-4 are shown in Table 9.

TABLE 9

Tablet hardness and tablet disintegration time (1) of actual examples 8-1 to 8-4, and controls 8-1 and 8-7

| (Single formula, granulation) | Excipient | Tablet hardness (kgf) | Tablet disintegration time (1) (min.) |
|---|---|---|---|
| Actual example 8-1 | Raw material 1 | 15.4 | 8.4 |
| Actual example 8-2 | Raw material 2 | 10.7 | 7.4 |
| Actual example 8-3 | Raw material 3 | 8.9 | 6.9 |

TABLE 9-continued

Tablet hardness and tablet disintegration time (1) of actual examples 8-1 to 8-4, and controls 8-1 and 8-7

| (Single formula, granulation) | Excipient | Tablet hardness (kgf) | Tablet disintegration time (1) (min.) |
|---|---|---|---|
| Actual example 8-4 | Raw material 4 | 8.6 | 6.8 |
| Control 8-1 | Mannit P | 6.0 | 9.0 |
| Control 8-7 | Lactose 200M | 7.2 | 14.7 |

Comparative Example 8

Single Formula, Granulation

The same method as in Example 8 was used to make tablets, except for the use of commercial products 1 and 7, instead of spherical particles of crystalline mannitol used in Example 8.

The values of tablet hardness and tablet disintegration time (1) about thus obtained controls 8-1 and 8-7 are shown in Table 9.

In the case of granulation without addition of starch, the actual examples of the present invention have proved harder in the tablet form and quicker to disintegrate, thereby achieving the compatibility of high hardness and quick disintegration.

Example 9

Standard Formula, Granulation 66.5 parts by weight of spherical particles of crystalline mannitol passing through a sieve having openings of 500 μm, 1.0 part by weight of ascorbic acid (100 M ascorbic acid, manufactured by BASF) passing through a sieve having openings of 500 μm, 28.5 parts by weight of corn starch (corn starch, manufactured by NIHON SHOKUHIN KAKO CO., LTD) passing through a sieve having openings of 500 μm, and 35.0 parts by weight of 10% aqueous solution of hydroxypropyl cellulose (HPC-L, manufactured by Nippon Soda Co., Ltd.) passing through a sieve having openings of 500 μm (3.5 parts by weight of hydroxypropyl cellulose on a solid basis) were mixed, granulated and dried in a fluidized-bed granulator (FLO-MINI, manufactured by OKAWARA MFG, CO., LTD.).

100 parts by weight of granulates thus obtained and, in addition, 0.5 parks by weight of magnesium stearate (manufactured by Wako Pure Chemical Industries, Ltd.) as a lubricating and glossing agent were processed into tablets, with tablet molds of 8 mm flat, unit weight of 180 mg, single pounder, as measured, at a rotational speed of 30 rpm, under a compressing force of 800 kgf.

The values of tablet hardness about thus obtained actual examples 9-1 to 9-4 are shown in Table 10.

TABLE 10

Tablet hardness of actual examples 9-1 to 9-4, and controls 9-1 and 9-7

| (Standard formula, granulation) | Excipient | Tablet hardness (kgf) |
|---|---|---|
| Actual example 9-1 | Raw material 1 | 11.6 |
| Actual example 9-2 | Raw material 2 | 8.8 |
| Actual example 9-3 | Raw material 3 | 7.7 |
| Actual example 9-4 | Raw material 4 | 7.2 |
| Control 9-1 | Mannit P | 5.5 |
| Control 9-7 | Lactose 200M | 5.9 |

Comparative Example 9

Standard Formula, Granulation

The same method as in Example 9 was used to make tablets, except for the use of commercial products 1 and 7, instead of spherical particles of crystalline mannitol used in Example 9.

The values of tablet hardness about thus obtained controls 9-1 and 9-7 are shown in Table 10.

To the standard formula of granulation accompanied with starch i.e. standard to assess an excipient, the actual examples have proved harder than the controls.

Now, applications of the excipient of the present invention to the conventional art will be explained in the following.

Example 10

Application of the Present Invention to the Conventional Art-1

Pursuant to Example 5 in Japanese Laid-Open Patent No. 2001-58944, page 9, column 15, line 23, the excipient of the present invention was used.

78.1 parts by weight of spherical particles of crystalline mannitol passing through a sieve having openings of 500 μm, 10.8 parts by weight of corn starch (corn starch, manufactured by NIHON SHOKUHIN KAKO CO., LTD) passing through a sieve having openings of 500 μm, 10.8 parts by weight of crystalline cellulose (CEOLUS PH101, manufactured by Asahi Kasai Chemicals Corporation) and 0.3 parts by weight of light anhydrous silicic acid (Aerosil-290, Japan Aerosil Co., Ltd.) were mixed, granulated and dried as ventilated in a fluidized-bed granulator (FLO-MINI, manufactured by OKAWARA MFG. CO., LTD.).

92.6 parts by weight of granulates obtained as above, passing through a sieve having openings of 710 μm and, 5.0 parts by weight of crospovidone (Kollidon CL, manufactured by BASF) as a disintegrating agent, 2.0 parts by weight of magnesium stearate (manufactured by Wako Pure Chemical Industries, Ltd.) as a lubricating and glossing agent, 0.1 part by weight of light anhydrous silicic acid (Aerosil-200, Japan Aerosil Co., Ltd.) and 0.3 parts by weight of aspartame (manufactured by AJINOMOTO CO., INC.) were processed into tablets, with tablet molds of 8 mm flat, unit weight of 180 mg, single pounder, as measured, at a rotational speed of 30 rpm, under compressing forces of 400, 700 and 1000 kgf.

The values of tablet hardness and tablet disintegration time (2) about thus obtained actual examples 10-1-1 to 10-4-3 are shown in Table 11 and FIG. 1.

TABLE 11

Tablet hardness and tablet disintegration time (2) of actual examples 10-1-1 to 10-4-3, and controls 10-1-1 to 10-1-3

| (Conventional formula-1, granulation) | Excipient | Compressing force (kgf) | Tablet hardness (kgf) | Tablet disintegration time (2) (sec.) |
|---|---|---|---|---|
| Actual example 10-1-1 | Raw material 1 | 400 | 3.9 | 19 |
| Actual example 10-1-2 | Raw material 1 | 700 | 8.8 | 23 |
| Actual example 10-1-3 | Raw material 1 | 1000 | 12.5 | 26 |
| Actual example 10-2-1 | Raw material 2 | 400 | 2.4 | 22 |
| Actual example 10-2-2 | Raw material 2 | 700 | 5.7 | 23 |
| Actual example 10-2-3 | Raw material 2 | 1000 | 7.9 | 20 |
| Actual example 10-3-1 | Raw material 3 | 400 | 2.4 | 17 |
| Actual example 10-3-2 | Raw material 3 | 700 | 5.5 | 21 |
| Actual example 10-3-3 | Raw material 3 | 1000 | 7.8 | 21 |
| Actual example 10-4-1 | Raw material 4 | 400 | 2.2 | 20 |
| Actual example 10-4-2 | Raw material 4 | 700 | 5.0 | 21 |
| Actual example 10-4-3 | Raw material 4 | 1000 | 6.9 | 22 |
| Control 10-1-1 | Mannit P | 400 | 0.8 | 20 |
| Control 10-1-2 | Mannit P | 700 | 1.6 | 24 |
| Control 10-1-3 | Mannit P | 1000 | 2.6 | 23 |

Comparative Example 10

Application to Conventional Art-1

The same method as in Example 10 was used to make tablets, except for the use of commercial product 1 instead of spherical particles of crystalline mannitol used in Example 10.

The values of tablet hardness and tablet disintegration time (2) about thus obtained controls 10-1-1 to 10-1-3 are shown in Table 11 and FIG. 1.

To use crospovidone as a disintegrating agent pursuant to Japanese Laid-Open Patent No. 2001-58944, actual examples kept higher hardness at the respective compressing forces than the controls, while more or less maintaining the disintegration time.

Example 11

Application of the Present Invention to the Conventional Art-2

The excipient of the present invention was used pursuant to Example 17 in international Publication No. WO2008/032767, page 16, line 22.

78.3 parts by weight of spherical particles of crystalline mannitol passing through a sieve having openings of 500 μm, 21.2 parts by weight of pregelatinized corn starch (corn starch, manufactured by NIHON SHOKUHIN KAKO CO., LTD) passing through a sieve having openings of 500 μm, overnight heat-treated at a temperature of 70° C., relative humidity of 80% in a constant temperature and high humidity bath, and 50 parts by weight of paste comprising 0.5 parts by weight of corn starch passing through a sieve having openings of 500 μm and 49.5 parts by weight of purified water heat-treated together (0.5 parts by weight on a solid basis) were mixed, granulated and dried as ventilated in a fluidized-bed granulator (FLO-MINI, manufactured by OKAWARA MFG. CO., LTD.).

94.5 parts by weight of granulates obtained as above, passing through a sieve having openings of 710 μm and, 5.0 parts by weight of crystalline cellulose (CEOLUS PH101, manufactured by Asahi Kasei Chemicals Corporation) and 0.5 parts by weight of magnesium stearate (manufactured by Wako Pure Chemical Industries, Ltd.) as a lubricating and glossing agent were processed into tablets, with tablet molds of φ8 mm 12 R, unit weight of 200 mg, single pounder, as measured, at a rotational speed of 30 rpm, under compressing forces of 400, 600 and 800 kgf.

The values of tablet hardness and tablet disintegration time (2) about thus obtained actual examples 11-1-1 to 11-4-3 are shown in Table 12 and FIG. 2.

TABLE 12

Tablet hardness and tablet disintegration time (2) of actual examples 11-1-1 to 11-4-3, and controls 11-1-1 to 11-1-3

| (Conventional formula-2, granulation) | Excipient | Compressing force (kgf) | Tablet hardness (kgf) | Tablet disintegration time (2) (sec.) |
|---|---|---|---|---|
| Actual example 11-1-1 | Raw material 1 | 400 | 3.3 | 28 |
| Actual example 11-1-2 | Raw material 1 | 600 | 6.1 | 32 |
| Actual example 11-1-3 | Raw material 1 | 800 | 9.5 | 35 |
| Actual example 11-2-1 | Raw material 2 | 400 | 4.0 | 22 |
| Actual example 11-2-2 | Raw material 2 | 600 | 6.9 | 26 |
| Actual example 11-2-3 | Raw material 2 | 800 | 9.5 | 30 |
| Actual example 11-3-1 | Raw material 3 | 400 | 3.4 | 24 |
| Actual example 11-3-2 | Raw material 3 | 600 | 5.9 | 27 |
| Actual example 11-3-3 | Raw material 3 | 800 | 8.8 | 31 |
| Actual example 11-4-1 | Raw material 4 | 400 | 3.1 | 20 |
| Actual example 11-4-2 | Raw material 4 | 600 | 5.2 | 23 |
| Actual example 11-4-3 | Raw material 4 | 800 | 6.6 | 26 |
| Control 11-1-1 | Mannit P | 400 | 1.5 | 18 |
| Control 11-1-2 | Mannit P | 600 | 2.8 | 18 |
| Control 11-1-3 | Mannit P | 800 | 4.2 | 21 |

Comparative Example 11

Application to the Conventional Art-2

The same method as in Example 11 was used to make tablets, except for the use of commercial product 1 instead of spherical particles of crystalline mannitol used in Example 11.

The values of tablet hardness and tablet disintegration time (2) about thus obtained controls 11-1-1 to 11-1-3 are shown in Table 12 and FIG. 2.

To use pregelatinized corn starch pursuant to International Publication No. WO2008-032767, actual examples kept higher hardness at the respective compressing forces than the controls, while more or less maintaining the disintegration time.

[Prior Art Documents]
[Patent Documents]
[Patent Document 1] Japanese Laid-Open Patent No. 6-205959
[Patent Document 2] Japanese Laid-Open Patent No. 62-265295
[Patent Document 3] Japanese Patent No. 3447042
[Patent Document 4] Japanese Patent No. 3491887
[Patent Document 5] Japanese Patent No. 3910939
[Patent Document 6] Japanese Laid-Open Patent No. 7-184590
[Patent Document 7] Japanese Laid-Open Patent No. 2004-2290

The invention claimed is:

1. An excipient for compressed tablets characterized in that it comprises spherical particles of crystalline mannitol having an aspect ratio of 1.0 to 1.2, and having according to Test A, an oil absorption rate 1 of 25 to 60% and an oil absorption rate 2 of 15 to 40%,
the spherical particles of crystalline mannitol having a mean diameter of 15 to 85 μm and, as a powder, a loose bulk density of 0.35 to 0.60 g/mL,
wherein the test method A comprises:
adding 30 g of middle chain fatty acid triglyceride and 15 g of the powder, (together referred to hereinafter as "the sample") to a 100 ml glass beaker;
stirring the sample with a spatula gently enough to avoid crushing of fine particles;
introducing the sample into a vacuum constant temperature dryer for three hours at a room temperature at a pressure reduced down to 0.67 pascals;
pouring the sample into a centrifuge tube having openings at bottom with a filter cloth of 325 meshes laid inside;
centrifuging the centrifuge tube containing the sample by a centrifuge for 10 minutes at about 1300 G;
obtaining the weight, in grams, of the powder remaining in the centrifuge tube after centrifugation ($W_1$);
placing the centrifuge tube containing the powder remaining after centrifugation into another 100 ml glass beaker and adding 20 g of n-hexane onto the powder,
centrifuging the centrifuge tube for 10 minutes at about 1300 G;
obtaining the weight, in grams, of the powder remaining in the centrifuge tube after the second centrifugation ($W_2$),
wherein the oil absorption rate 1 and the oil absorption rate 2 are given the following formulas:

$$\text{oil absorption rate 1}(\%) = [(W_1 - 15)/15] \cdot 100$$

$$\text{oil absorption rate 2}(\%) = [(W_2 - 15)/15] \cdot 100.$$

2. An excipient for compressed tablets according to claim 1, characterized in that it comprises spherical particles of crystalline mannitol having an angle of repose of 30 to 50 degrees, as a powder.

3. An excipient for compressed tablets according to any one of claim 1 or 2, characterized in that the spherical particles of crystalline mannitol are made by spray drying.

* * * * *